US 8,343,758 B2

(12) United States Patent
Cheema et al.

(10) Patent No.: US 8,343,758 B2
(45) Date of Patent: Jan. 1, 2013

(54) BIO-ARTIFICIAL MATERIALS WITH TUNEABLE PROPERTIES

(75) Inventors: Umber Cheema, Middlesex (GB);
Cher-Bing Chuo, Birmingham (GB);
Robert Brown, Middlesex (GB)

(73) Assignee: ULC Business PLC, London (GB)

(*) Notice: Subject to any disclaimer, the term of this patent is extended or adjusted under 35 U.S.C. 154(b) by 1135 days.

(21) Appl. No.: 12/094,971

(22) PCT Filed: Nov. 24, 2006

(86) PCT No.: PCT/GB2006/004414
§ 371 (c)(1),
(2), (4) Date: May 23, 2008

(87) PCT Pub. No.: WO2007/060459
PCT Pub. Date: May 31, 2007

(65) Prior Publication Data
US 2008/0286244 A1    Nov. 20, 2008

(30) Foreign Application Priority Data

Nov. 25, 2005 (GB) .................................. 0524048.6

(51) Int. Cl.
*C12N 5/07* (2010.01)
(52) U.S. Cl. ..................... 435/325; 424/93.7; 424/422
(58) Field of Classification Search ............... 424/93.7, 424/422; 435/325
See application file for complete search history.

(56) References Cited

U.S. PATENT DOCUMENTS

| | | | |
|---|---|---|---|
| 4,689,399 A | 8/1987 | Chu | |
| 4,772,419 A | 9/1988 | Mälson et al. | |
| 5,718,012 A * | 2/1998 | Cavallaro | 8/94.11 |
| 2002/0106625 A1 | 8/2002 | Hung et al. | |
| 2002/0159982 A1 | 10/2002 | Bonassar et al. | |
| 2004/0054372 A1 | 3/2004 | Corden et al. | |
| 2006/0014284 A1 * | 1/2006 | Graeve | 435/397 |
| 2006/0273279 A1 | 12/2006 | Kaplan et al. | |

FOREIGN PATENT DOCUMENTS

| | | |
|---|---|---|
| WO | WO 97/11724 A1 | 4/1997 |
| WO | WO 97/45071 | 12/1997 |
| WO | WO 02/051463 A2 | 7/2002 |
| WO | WO 03/080141 | 10/2003 |
| WO | WO 2005/046457 A2 | 5/2005 |
| WO | WO 2006/003442 | 1/2006 |
| WO | WO 2006/042287 A2 | 4/2006 |
| WO | WO 2006/115892 A2 | 11/2006 |
| WO | WO 2007/060459 A2 | 5/2007 |

OTHER PUBLICATIONS

Yonekura et al., "Effects of cyclic loading frequency on mechanical properties of cultured regenerated ligament-like tissue" *Proceedings, 16th Biofrontier Symposium, Japan Society of Mechanical Engineers*, 2005, Kusatsu, Japan (No. 05-53) (7 pages) (translated from Japanese by the Japan Patent Office).
Cacou et al., "A system for monitoring the response of uniaxial strain on cell seeded collagen gels," *Medical Engineering & Physics*, 22:327-333, 2000.
Garvin et al., "Novel System for Engineering Bioartificial Tendons and Application of Mechanical Load," *Tissue Engineering*, 9 (5):967-979, 2003.
Murayama et al., "Effects of cyclic load on the mechanical properties of cultured ligament-like tissue," *Proceedings of Biofrontier Symposium*, 16:25-26 2005 (in Japanese, with English Abstract).
Takakuda et al., "Strengthening of Fibrous Tissues under Mechanical Stimuli (in vitro Experiments)," *JSME International J. Series A*, 41 (4):576-583, 1998.

* cited by examiner

*Primary Examiner* — Ruth Davis
(74) *Attorney, Agent, or Firm* — Klarquist Sparkman, LLP

(57) ABSTRACT

This invention relates to methods for preparing biomaterials by applying multiple cycles of tensile loading to compacted collagen gels in order to fuse the collagen fibrils together within the compacted gels. This produces a biomaterial with improved material properties. Biomaterials produced by such methods may be useful, for example, as tissue equivalent implants, in the repair and/or replacement of damaged tissue in an individual.

23 Claims, 7 Drawing Sheets

BIO-ARTIFICIAL MATERIALS WITH TUNEABLE PROPERTIES

CROSS REFERENCE TO RELATED APPLICATIONS

This is the U.S. National Stage of International Application No. PCT/GB2006/004414, filed Nov. 24, 2006, which was published in English under PCT Article 21(2), which in turn claims priority to Great Britain Patent Application No. 0524048.6, filed Nov. 25, 2005. Both applications are incorporated herein in their entirety.

This invention relates to methods for preparing bio-artificial materials and tissue equivalent implants for use in the repair and/or replacement of damaged tissue in an individual, and biomaterials and implants produced by such methods.

The mechanical (i.e. functional) properties of most connective tissues are governed by the fibrous protein collagen and its 3D architecture. Since most of the chronic, age-related, sports, surgical and trauma injuries of modern Western populations involve these connective tissues, failure of collagen function represents arguably the most important clinical factor affecting life quality and mobility. As a result, the majority of the major new developments towards tissue engineering and regenerative medicine aim to rebuild or induce regeneration of collagen structures (R. A. Brown, in *Future Strategies for Tissue and Organ Replacement* (Eds: J. M. Polak, L. L. Hench, P. Kemp), World Scientific Publishing, Singapore (2002) 48; R. A. Brown et al *Wound Rep. Reg.* (1997) 5 212). A key limitation to progress in treatments is the poor understanding of how collagen fibril architecture and particularly fibril diameter is regulated by cells.

Fibril architecture (as for any fibrous material) is central to the material properties of collagen structures. At the moment, all therapeutic approaches to the reconstruction of even simple, partially functional (replica) tissues employ cellular activity to rebuild collagen structure (M. Eastwood et al, *Cel. Motil. Cytoskel.* 1998 40 13; D. Huang, et al *Ann. Biomed. Eng.* 1993 21 289). This limits the engineering of tissues both in vivo during repair and in vitro for growth of graft tissues. This poor understanding also restricts the development of new therapeutic approaches to diseases or failed repair processes in patients. Examples are the arthritides, neuro-muscle injury/degeneration, musculo-tendenous failure and age-degeneration, poor regeneration after trauma, tissue necrosis or surgical resection (e.g. tumour surgery).

A key problem in tissue engineering remains the inability to control or influence tissue material properties to produce specific patterns of collagen fibril structures, without the use of cells.

The present inventors have discovered that applying multiple cycles of tensile loading to compacted collagen gels causes collagen fibrils to fuse together within the compacted gel. This fusion leads to improved material properties, without the involvement of cells.

One aspect of the invention provides a method of producing a biomaterial comprising;
 (i) plastically compacting a collagen gel,
 (ii) applying a uniaxial tensile load to the compacted gel,
 (iii) removing said load, and;
 (iv) repeating steps (ii) and (iii) to produce said biomaterial.

Repetitive cycles of loading increase the fusion of collagen fibrils in the compacted gel to produce a biomaterial which has improved material strength (i.e. increased break stress, break strain and/or elastic modulus). The biomaterial produced may be useful for example in the production of a tissue equivalent implant.

Increased fusion of fibrils in the gel may lead to an increase in fibril diameter or an increase in the number, size and/or tightness of intersection anastomoses in the network of fibrils.

A collagen gel for use as described herein comprises a matrix of collagen fibrils which form a continuous network around an interstitial fluid. Methods for the production of collagen gels are well-known in the art. For example, triple-helical collagen monomers may be initially dissolved in dilute acid and then induced to polymerise (aggregate) to fibrils (e.g. at 37° and neutral pH). As the fibrils polymerise, there is a phase change and the solid network of fibrils 'supports' the remaining interstitial liquid in approximately the same volume and shape—i.e. it gels. Phase transition from soluble monomer to solid polymer is characteristic of a gel. Collagen gels as described herein are distinct from 'sponges' formed from pre-polymerised fibres or other insoluble aggregates of collagen fibres and are also distinct from gels made from denatured collagen, such as gelatin.

Collagen fibrils may be of any native fibril-forming collagen type, including collagen types I, II, III, V, VI, VII, IX and XI and combinations of these (e.g. I, III V or II, IX, XI etc). More preferably, the collagen fibrils are of collagen type I, II or III. For example, the fibrils may be collagen type I fibrils.

The interstitial liquid is typically an aqueous liquid, although other organic solvents may be used in certain abiotic applications. For example, the liquid may be water with solutes, such as salts and proteins, dissolved therein. In some embodiments, the interstitial liquid is a cell culture medium suitable for the growth and proliferation of cells.

In some embodiments, the collagen gel may be acellular and devoid of viable cells. In other embodiments, the gel may comprise viable cells that may, for example, confer tissue functionality in the produced biomaterial and provide structures that replace or facilitate the repair of endogenous tissue. For example, the gel may comprise one or more of muscle cells to provide contractile structures, vascular and/or neural cells to provide conductive elements, metabolically active secretory cells, such as liver cells, hormone synthesising cells, sebaceous cells, pancreatic islet cells or adrenal cortex cells to provide secretory structures, stem cells, such as adult tissue derived (e.g. bone marrow) or embryonic stem cells, dermal fibroblasts, skin keratinocytes, (and combination layers of the two), Schwann cells or other glial cell types for nerve implants, smooth muscle cells and endothelial cells for vessel structures, urothelial and smooth muscle cells for bladder/urethra structures and osteocytes, chondrocytes, and tendon cells for bone and tendon structures. In some embodiments, the cells seeded into the gel may include fibroblasts.

Cells may be distributed interstitially within the gel in any arrangement. For example, the cells may be distributed homogeneously throughout the gel or distributed in defined zones, regions or layers within the gel. The cells are preferably seeded into the gel before compaction, for example by mixing them with the liquid collagen, for example at a cell density of at least $1 \times 10^5$ cells per ml, and then allowing the collagen to solidify into a gel, in accordance with known techniques. Seeding of the collagen matrix is preferably performed under suitable conditions of temperature, pH, ionic strength and shear to maintain viability, prior to gel formation. The cells may be incubated in the gel for 24 hours or less, 12 hours or less, 6 hours or less, 3 hours or less, or 1 hour or less, most preferably 0 to 2 hours before compaction.

The collagen gel is plastically compacted as described herein to bring the fibrils of the gel into close proximity and facilitate fibril fusion.

Plastic compaction of a gel comprises deforming the gel to reduce its volume, such that the gel retains or substantially retains its new volume, even after the cause of compaction is removed. Plastic compaction of a collagen gel reduces the distance between collagen fibrils and increases the number of contact points between adjacent fibrils. Plastic compaction is a rapid, cell-independent process which results from subjecting the gel to a physical treatment, such as an external force or pressure, which expels interstitial liquid from the gel. Plastic compaction is distinct from the slow process of cell-driven contraction, which occurs through the intrinsic action of cells growing within the gel i.e. plastic compaction is not cell-mediated and does not occur through the action of cells which are cultured within the gel.

Compaction of the gel, for example by compression, may result in a reduction in one or more dimensions of the gel of at least 5 fold, at least 10 fold or at least 20 fold. The one or more dimensions may be reduced by 500 fold or less, 300 fold or less, 200 fold or less, 150 fold or less, or 100 fold or less. In preferred embodiments, the thickness of the gel is reduced by compaction.

For example, the volume of the gel may be reduced by 50% or more, 60% or more, 70% or more, 80% or more, 90% or more, 95% or more, 99% or more, or 99.9% or more by plastic compaction.

Plastic compaction occurs over a shorter time than the time required for cell-driven contraction to occur and may vary in accordance with the compaction method and the conditions used. For example, compaction may occur in less than 12 hours, less than 6 hours, less than 3 hours, less than 1 hour, less than 30 minutes or less than 10 minutes. In some preferred embodiments, the gel may be compacted in 2 minutes or less or 1 minute or less.

Plastic compaction of the gel may be associated with the loss or removal of interstitial fluid from the gel. For example, the amount of fluid lost or removed from the gel by plastic compaction may be at least 50%, at least 60%, at least 70%, at least 80%, at least 90%, at least 99%, or at least 99.9% of the original fluid content of the gel.

The gel may be plastically compacted by any convenient means or combination of means. Suitable techniques and protocols for the plastic compaction of collagen gels are described in PCT/GB2005/002631. In some preferred embodiments, a mechanical force, such as a compressive force, may be applied to the gel. The amount of compressive force applied to the gel to achieve the desired compaction depends on the particular circumstances and may be readily determined by the skilled person. For example, a suitable compressive force may be 0.1 to 10 N, e.g. 1 N. Preferably, the gel is unconfined when subjected to the compressive force. Any suitable method of applying a compressive force to the gel may be employed. For example, a gel may be compressed by one or more of: applying a static load (for example a dead weight) to the gel, applying a load through a hydraulic or cam or passing the gel through rollers.

In some embodiments, fluid pressure hydration expansion may be used to compact the collagen gel.

In some embodiments, the fibrils of the compacted gel may be unordered and may be in a random network arrangement prior to cyclical loading, with no alignment in any dimension. Cyclical loading increases the strength of the network of fibrils by increasing the number, size and tightness of intersection anastomoses and may be used to produce substantially isotropic biomaterials.

In other embodiments, the fibrils of the compacted gel may be partially or wholly aligned prior to cyclical loading. For example, the fibrils may show alignment or orientation in one dimension (e.g. aligned or parallel layers or planes of fibrils which are randomly orientated within each layer) or, more preferably, in two dimensions (i.e. aligned or parallel layers or planes of fibrils which are aligned or parallel within each layer).

Collagen fibrils may be aligned using any convenient technique. Many suitable techniques are known in the art. For example, the ends of the gel may be clamped and a uni-axial strain applied between the clamped ends (see for example M. Eastwood et al, Cel. Motil. Cytoskel. (1998) 40 13; Mudera et al (ibid) 2000; and Marenzana et al Exp. Cell. Res. (In press)); the gel may be subjected to shear force and angled gelling (Elstow & Bard. J. Biol. Chem. 1976); or collagen fibrils may be gelled under ultra high magnetic fields (Kotani H, et al (2000) J. App. Phys 87 6191-3, Torbet J et al Biochem J. (1984) 219:1057, Guido S et al J. Cell. Sci. 105:317 (1993)).

The tension which is applied during the loading cycles may provide sufficient alignment to the fibrils. Alternatively, tension may be applied to the gel as a separate step before cyclical loading (step ii). For example, a static uniaxial tension may be applied to the gel before cyclical loading which subjects the compacted gel to 5-50% uniaxial strain, preferably 10-30% or 20-25% uniaxial strain, such that the collagen fibrils and, if present, seeded cells, align in a parallel orientation to the direction of principle strain. The rate of loading of a separate aligning tension may be faster than the rate of cyclical loading. In some embodiments, the rate of loading of the separate aligning tension may be sufficiently high to promote plastic deformation of the gel.

The tension may be applied after or, more preferably, before the gel is plastically compacted. Alternatively, the tension may be applied during plastic compaction, for example at the start of the plastic compaction process or part way through (e.g. 20 to 60% compression), and then returned to the plastic compaction regime, such that the fibril alignment induced by the tensile strain is fixed into the gel, giving an aligned dense composite.

Following plastic compaction and, optionally, alignment or orientation of collagen fibrils, the collagen gel may be subjected to multiple cycles of tensile loading. This cyclical loading causes the collagen fibrils in the gel to move relative to each other, bringing the surface charge motifs of adjacent fibrils into register and thus allowing the fibrils to fuse. The fusion of adjacent fibrils within the collagen gel leads to the formation of fibrils of increased diameter within the gel. The direction of loading (i.e. the load vector) may determine which fibrils in the gel increase in diameter, as fibrils parallel to the load axis increase their diameter more than fibrils perpendicular to the load axis. In embodiments in which the fibrils of the gel are pre-aligned, the direction of loading preferably corresponds to the direction of the fibril alignment.

Each cycle of tensile loading comprises a loaded phase in which a uniaxial tensile load is applied to the compacted gel and an unloaded phase in which the tensile load is removed.

The loaded phase of each loading cycle may comprise a ramped loading period and, optionally, a stress relaxation period. The load applied to the gel is progressively increased to a predetermined value in the ramped loading period. The load applied to the gel may then be maintained at the predetermined value in the stress relaxation period.

The tensile load applied to the gel is preferably increased at a rate such that the deformation caused is viscoelastic and temporary (i.e. non-plastic deformation). For example, the load may be increased or ramped up over a period of 1 min or more, 5 min or more, 10 min or more, 15 minutes or more or 30 minutes or more. Suitable rates of loading include 10% strain/min or less, 5% strain/min or less, 4% strain/min or less, 3% strain/min or less, 2% strain/min or less, 1% strain/min or less.

Methods for applying a tensile load to a gel are well-known in the art as described above (see for example, M. Eastwood et al, *Cell. Motil. Cytoskel.* (1998) 40 13). In some preferred embodiments, the ends of the collagen gel may be clamped and a uniaxial load applied between the clamped ends.

Other suitable methods include magnetic pull, osmosis, compression, fluid hydration expansion, and fluid shear. Fluid shear may particularly useful in applying tensile loading to collagen gels that are in the form of particles, vesicles, beads or powders.

Fluid flow may also be useful in applying a load to a compacted collagen gel, for example a tubular construct comprising a compacted collagen gel which is spiralled or rolled around a swellable core. A swellable core may comprise a component which expands or swells on hydration, for example a gel-forming, charged compound with large swelling pressure, such as hyaluronan, starch, dextran, chitosan and glycoaminoglycans such as chondroitin sulphate, keratin sulphate and heparin. Hydration of the core (e.g. by wetting) causes it to expand, thereby applying a tensile load to the surrounding collagen. The load is then removed or dissipated as the swollen core material breaks down or diffuses away, leaving a central channel surrounded by compacted collagen layers. Cyclical loading may be applied to such a construct as described above to promote longitudinal fibril fusion or, alternatively, circumferential fibril fusion may be promoted by applying pulsatile fluid flow through the central channel.

A suitable tensile load for cyclical loading may subject the gel to at least 5%, 10%, 15% or 20% strain and up to 30%, 40% or 50% strain. Typically, a suitable tensile load may subject the gel to 20% strain. In some embodiments, a tensile load may be employed which is 5% below the break strain of the gel.

In some embodiments, after the tensile load has reached the predetermined value, it may be progressively reduced or removed in the unloaded phase of the loading cycle. In other embodiments, the loaded phase of the loading cycle may further comprise a period of stress relaxation in which the load of the predetermined value is continuously applied to the gel for a period of 10 s or more, 30 s or more, 1 min or more, 5 mins or more, 10 mins or more, 15 mins or more, or 30 mins or more.

Following the loaded phase, the tensile load may be removed from the gel in the unloaded phase of the loading cycle. The unloaded phase of the loading cycle may comprise a ramped unloading period, in which the tensile load applied to the gel is progressively removed.

The tensile load is preferably reduced at a rate which is sufficient to allow the gel to return to its original shape and may be varied, depending on the material density and the stiffness during loading. For example, the load may be decreased or ramped down over a period of 1 min or more, 5 mins or more, 10 mins or more or 15 mins or more. Suitable rates of unloading include 10% strain/min or less, 5% strain/min or less, 4% strain/min or less, 3% strain/min or less, 2% strain/min or less, 1% strain/min or less.

Optionally, the unloaded phase may also comprise a period of relaxation during which the gel is maintained unloaded or under a reduced load, following removal or reduction of the tensile load. The gel may, for example, be maintained in a relaxed state (e.g. unloaded, or substantially unloaded) for a period of 10 s or more, 30 s or more, 1 min or more, 5 mins or more, 10 min or more, 15 mins or more, or 30 minutes or more.

Following removal or reduction of the tensile load from the compacted gel, and optionally a relaxation period, the load may be progressively increased in the loaded phase of the next cycle of loading.

In some preferred embodiments, a suitable loading cycle may comprise ramped loading over 5 mins to a predetermined load such as 20%, for example at a steady rate of 4%/min, stress relaxation at 20% strain for 5 mins, followed by a ramped unloading over 5 mins, for example at a steady rate of 4%/min to an unloaded state which is maintained for 5 mins before the next cycle of loading.

The loading cycle (i.e. steps (ii) and (iii)) may be repeated 2 or more times, 10 or more times, 50 or more times, 100 or more times or 200 or more times.

The load and non-load phases may be repeated at a rate of 0.1, 0.5, 1, 2, 3, 4, 5, 6, 7, 8, 9, 10 or more times per hour. In some preferred embodiments, the loading cycles may be repeated at a rate of less than 10 cycles per hour.

It will be appreciated that the number of loading cycles, the rate of cycling and the parameters of each cycle (e.g. the amount of load, rate of loading and the length of the load and non-load phases) may be varied by the skilled person according to the stiffness of the collagen gel at any given time and the precise biomaterial properties required.

In some embodiments, for example, the parameters of loading and non-loading may be kept constant throughout the loading cycles. In other embodiments, it may be convenient to alter the loading and non-loading parameters during the loading cycles.

For example, the cycling rate may be altered e.g. increased or decreased during the loading cycles; in particular the rate may be increased as the stiffness of the compacted gel increases. Similarly, the strain which is applied to the gel may be progressively increased. For example, in some embodiments, initial loading cycles may be performed at low rate and high strain (e.g. 20-30% at 3-30 cycles/hour), followed by longer periods of cycles at high rate and low strain (e.g. 5% strain at 50-100 cycles/hour).

The compacted gel may also be subjected to cycles of gentle, slow compression or fluid shear to improve or modify surface properties.

In cellular embodiments, the compacted gel is preferably maintained at physiological conditions throughout the methods described herein (e.g. temperature, pH, hydration and ionic strength) for the cells to survive. To reduce cell death and/or damage associated with desiccation, the gel may be compacted and subjected to cyclical loading in an aqueous liquid, for example a culture medium, such as DMEM, Ham's or Eagle's medium or a physiological buffer such as Ringer's or PBS at a suitable temperature, for example 5° C. to 37° C.

In abiotic or acellular embodiments, the compacted gel need not maintained at physiological conditions and any method of plastic compaction and cyclical loading and any solvent compatible with the scaffold matrix may be used, including those that alter the ionic properties of the gel fluid, such as osmotic methods.

The properties of the biomaterial produced by the present methods may be adjusted for a particular usage or application by varying the ratios of individual constituents (e.g. in % v/v) in the collagen gel, the parameters of compaction and the number and parameters of the loading cycles. For example, the proportion of collagen may be altered to change the strength of a biomaterial, the cyclical loading may be altered to vary the diameter of the collagen fibrils, the proportion of cells may be altered to change the cell activity of a biomaterial and/or the presence or amount of microchannelling may be altered to change the perfusion properties of the biomaterial.

A compacted collagen gel whose fibril diameter and mechanical properties have been improved by cyclical loading as described herein may be useful as a biomaterial, for example a biomimetic or bioartificial material suitable for use in the production of a tissue equivalent implant.

Biomaterial produced by the present methods may be in any convenient form, for example, it may be a sheet, ring, toroid, capillary, strip, block, tube, particle, or roll.

In some embodiments, the biomaterial produced by the present methods may be useful as a tissue equivalent implant for the repair or replacement of damaged tissue without additional processing.

In other embodiments, additional processing of the biomaterial may be performed to produce a tissue equivalent implant for the repair or replacement of damaged tissue. The biomaterial may, for example, be moulded and/or shaped to produce a tissue equivalent implant. The biomaterial may be moulded into a predetermined shape and/or may be subjected to further plastic compaction. Plastic compaction may be symmetrical or asymmetrical.

The biomaterial may be shaped or moulded into any convenient implant form, for example, a patch, block, tube, tape, strip, ring, toroid, capillary, roll, sheet or thread. The final shape of the tissue equivalent implant will depend on the particular context in which it is to be used. In some embodiments, the tissue equivalent implant may have a pliable form which is suitable for further shaping.

A sheet or strip of biomaterial produced by the present methods may be rolled up or folded to form a multi-layered construct e.g. a roll.

The rolled or folded multi-layered construct may be used directly as a tissue equivalent implant or may be further cut, shaped or moulded as required. In some embodiments, the construct may be plastically compacted further to adhere the layers together, achieve the desired dimensions, increase cell density or to improve other properties. This is described in more detail in PCT/GB2005/002631. This allows the rapid assembly of 3-dimensional tissue equivalent implants, which may for example be conveniently handled by a surgeon, from one or more flat 2-dimensional layers of biomaterial. The present invention allows such tissue equivalents to be given tuneable matrix architecture and mechanical properties (at the nano-/micro-scale) rapidly and without substantially harming cells contained within them.

A tissue equivalent implant is a material for implantation into an individual to repair or replace endogenous tissue, which, for example, may be damaged or diseased. Examples of diseased tissues which may be repaired or replaced by tissue equivalent implants include nerve, tendons, cartilage, skin, bone, urogenital elements, liver, cardiopulmonary tissues, kidney, ocular tissues, blood vessels, intestine, and glands.

Diseased or damaged tissue may for example result from arthritides, neuro-muscle injury/degeneration, musculo-tendenous failure and age-degeneration, poor regeneration after trauma, tissue necrosis or surgical resection (e.g. tumour surgery).

Following production as described above, the tissue equivalent implant may be implanted immediately into an individual or stored or subjected to further processing to modulate subtle properties of the collagen such as stiffness, elastic modulus etc.

To reduce and/or prevent cell death or damage, an implant or biomaterial comprising viable cells may be stored under conditions which maintain viability but which do not support cell growth, until ready for use. For example, the implant or biomaterial may be stored at low temperature, such as 0 to 5° C., preferably 4° C. In some embodiments, the biomaterial is not subjected to drying or desiccation, for example heat-, freeze-, airflow or vacuum drying, following plastic compaction and cyclical loading, as dehydration kills cells and damages biomaterial structure.

Another aspect of the invention provides a biomaterial produced by a method described herein.

The biomaterial preferably has improved properties relative to the compacted collagen gel or collagen based biomaterials produced by other means. For example, the biomaterial may have increased fibril diameter, increased material strength, reduced pore size, increased numbers of fibril cross-over points and increased stability of fibril crossover points.

Another aspect of the invention provides a tissue equivalent implant comprising or consisting of a biomaterial produced by a method described herein.

Another aspect of the invention provides a method of treatment of a damaged tissue in an individual comprising;

fixing a tissue equivalent implant as described herein to said damaged tissue to repair and/or replace said tissue.

The implant may be fixed by any convenient technique. For example, it may be sutured or glued in place.

Implants produced from the biomaterials described herein will take sutures and can be sutured surgically into body sites even when under muscle load.

Related aspects of the invention provide a tissue equivalent implant for use in a method of treatment of a damaged tissue in an individual and the use of a tissue equivalent implant in the manufacture of a medicament for use in the treatment of damaged tissue.

Damaged tissue in an individual may, for example result from arthritides, neuro-muscle injury or degeneration, musculo-tendenous failure and age-degeneration, poor regeneration after trauma, tissue necrosis or surgical resection (e.g. tumour surgery).

The present methods allow the organisation, architecture and fibril geometry of collagen-based biomaterials to be controlled and manipulated without dependence on cells. Biomaterials produced by the present methods may be useful as defined models of natural tissues (for example for research, teaching, clinical diagnosis, toxicity testing) or as standard materials or phantoms, for example in the calibration of optical/spectroscopic microscope, X-ray and MRI monitoring systems.

The present methods allow the pore size and therefore the ultrafiltration properties of biomaterials to be controlled and manipulated. Biomaterials produced as described herein may therefore be useful, for example, as filters with tuneable properties or in systems for controlled drug release.

Various further aspects and embodiments of the present invention will be apparent to those skilled in the art in view of the present disclosure. All documents mentioned in this specification are incorporated herein by reference in their entirety.

The invention encompasses each and every combination and sub-combination of the features that are described above.

Certain aspects and embodiments of the invention will now be illustrated by way of example and with reference to the figures and tables described below.

FIG. 1 shows frequency-plot showing the effect of increasing cycle number on the distribution pattern of collagen fibril diameters in the treated materials. There is approx 2 fold increase in median diameter across this range of treatments and a complete elimination of the smallest fibril species (15 to 40 nm diameter) present in the initial gels.

FIG. 2 shows a box and whisker plot of fibril diameter distribution. Boxes indicate inter-quartile range ($25^{th}$ to $75^{th}$ percentile), with middle lines representing median values. Error bars indicate total range of sizes.

Figure 6:
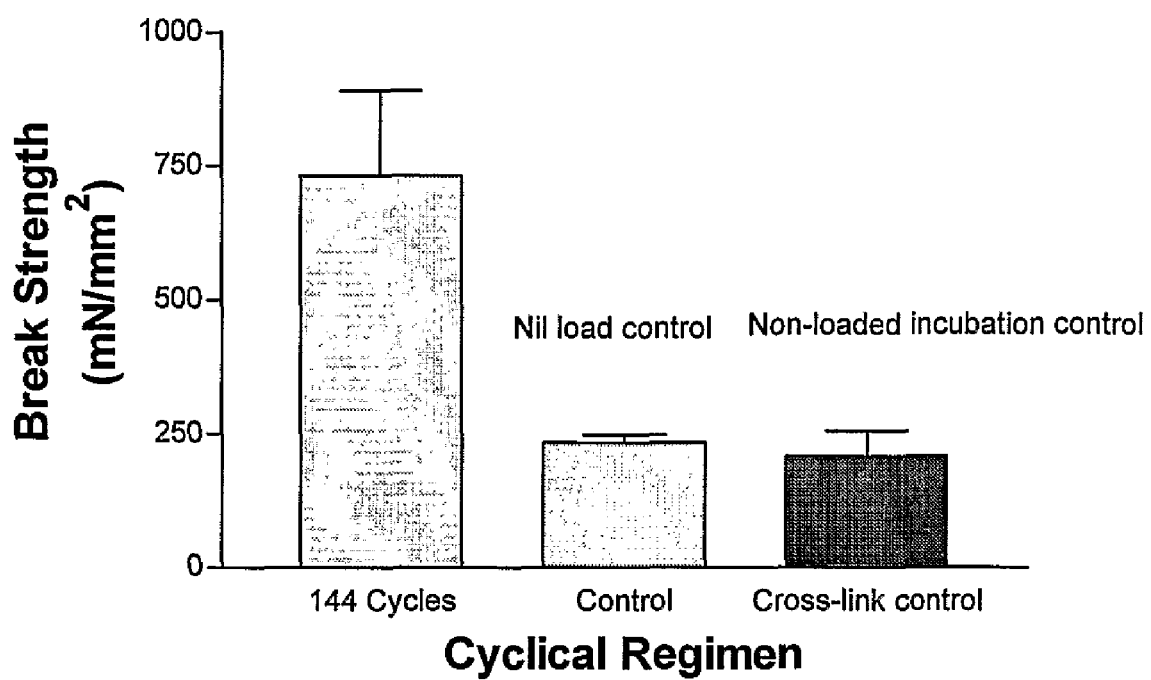

FIG. 6 shows the mean break strength of collagen gels following either 144 cycle of load, no loading control and collagen gels incubated under static tension for the same time as needed for 144 cycles. The 'incubation only' control was left for 48 h to incubate as for the 144 cycle series but without cyclical loading to test for spontaneous, time-dependent stabilization (if any), which might have occurred by spontaneous cross-link formation in the collagen. No increase in strength so no increase in cross-linking was seen in this control, showing the requirement for cyclical loading.

Figure 7:
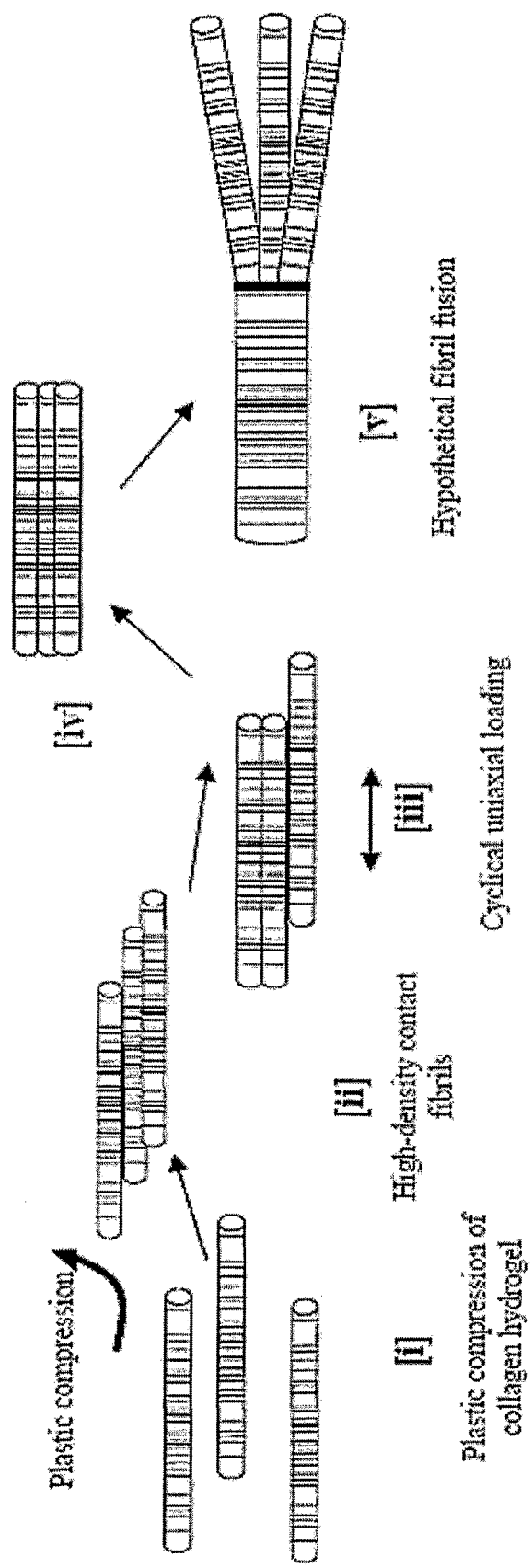

FIG. 7 shows a potential mechanism for mechanically mediated collagen fibril anastomosis. Firstly, sparse fibrils (formed by spontaneous monomer aggregation into a gel) are brought into close contact, by compaction [i]. This provides many points of fibril lateral contact, but very few where adjacent fibrils [ii] are in 'surface charge' register (indicated here as the fibril banding pattern seen at the EM level). However, application of cyclical uniaxial tensile strain leaves increasing numbers of adjacent fibrils in register [iii]. Fibrils which are both in contact and in register form stable anastomoses, resulting in progressive accumulation of linkages [iv] and so thicker fibril populations [v]. Importantly, increases in fibril diameter are incremental, as multiples of discrete fibril diameters. Ultrastructural analysis showed all phases of fibril fusion were found in transverse section 1) dumbbell 2) cloverleaf 3) larger circular cross sections with loss (progressive with more cycles) of small fibrils (20-30 nm). In longitudinal cross section, examples were found where 2, 3, or 4 separate fibrils merged into one larger fibril with a single banding pattern.

Figure 8:
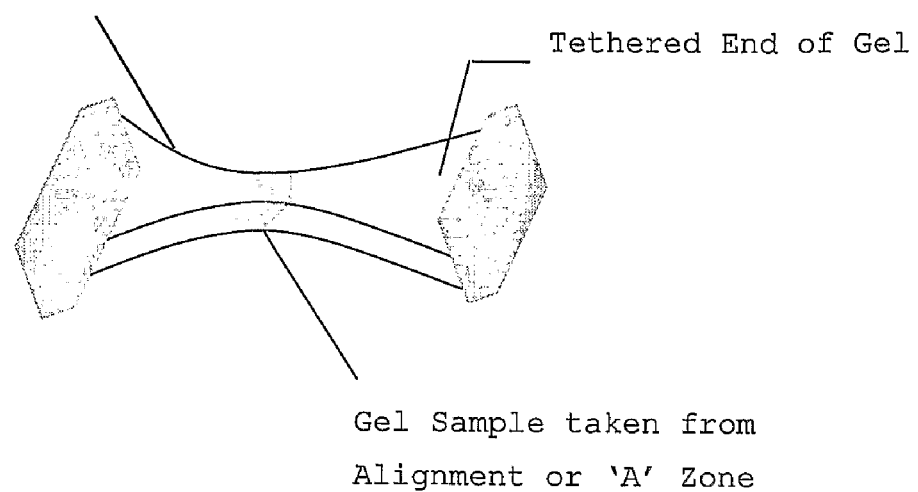

FIG. 8 shows collagen gels attached to two polyethylene mesh flotation bars for cyclical loading.

Table 1 shows the effect of cyclically loading on the mechanical properties of compressed collagen gels. Break stress is shown to increase 4.5 fold after 144 cycles.

Table 2 shows the distribution of orientation of collagen fibrils in the gel. Fibrils were grouped into the following categories: (i) transverse section (ie. parallel to the applied principal strain), (ii) oblique section (i.e. at an angle) and (iii) longitudinal section (ie. perpendicular to strain).

EXPERIMENTAL

Formation of Acellular Collagen Gels

Acellular collagen gels were made by the pH titration of type I collagen. For collagen gel preparation, 0.3 ml of 10X Eagles MEM solution (Gibco, Paisley, UK) and 0.3 ml of Dulbeccos modified eagles medium (Gibco) were added to 2.4 ml of rat tail type I collagen (in acetic acid, protein concentration=2.14 mg/ml, First Link, Birmingham, UK). This solution was neutralised with 5M NaOH, until a colour change was observed (yellow to cirrus pink) (Prajapati et al. 2000 Wound Rep. Regen. 8 227-238; Prajapati et al. 2000 Wound Rep. Regen. 8 239-247). This collagen gel was allowed to set in a well (22 mm×33 mm×10 mm) at room temperature for 30 minutes.

Plastic Compression

Following setting, collagen gels were compacted by 93%, using a standardised plastic compression protocol modified from Brown et al. (2005) Adv. Funct. Mater. 15, 1762-70. Collagen gels were placed between two sheets of nylon mesh (35 mm×70 mm), with the bottom layer laid on a stainless steel mesh, which in turn was laid on a single layer of Whatman grade I filter paper. A 125 g weight was then laid on the top of the gel for 5 minutes. Following this, the compacted gel was cut into three longitudinal strips of 7 mm×33 mm.

Mechanical Loading: Application of Cyclical Loading

The three sections of collagen gel were then attached to two polyethylene mesh flotation bars using cyanoacrylate glue, which in turn were attached to stainless-steel wire A-frames (FIG. 8). The collagen gels were then submerged in Earls' Balanced salt solution (EBSS) (Gibco), and placed in a humidified incubator with 5% $CO_2$. One A-frame was attached to a fixed point and the other to a force transducer, which was able to monitor the force and loading (Eastwood et al. 1996 J. Cell Physiol. 166: 33-42; Brown et al. (1996) J. Cell Physiol. 169:439-447). A computer controlled microstepper motor enabled exogenous loads to be applied to the acellular collagen gels.

Culture (t-CFM) Set-up

Compressed collagen gels were cast between two flotation bars, which were in turn attached to stainless steel wire A-frames (FIG. 8). These A-frames allowed a connection between the collagen gel and the t-CFM systems. One A-frame was fixed and the other attached to a force transducer, which monitored force and loading (Eastwood et al. 1998 Cell Motility Cytoskel. 49: 13-21). The analogue output signal was amplified, digitised and processed through 'Labview' program (National Instruments, Berkshire, UK). A computer-controlled micro stepper motor, acting in a plane parallel to the tethered axis of the collagen gels, enabled exogenous loads to be applied to the cultures.

Cyclical Loading Regimens

Various cyclical loading regimens were applied, with each cycle lasting 20 minutes (i.e. 3/3600 Hz). Each cycle consists of 4 equal phases (each lasting 5 minutes). Phase 1 was the linear application of 20% strain (total displacement of 6.6 mm of a 33 mm construct); phase 2 was holding at 20% strain; phase 3 was the release of strain; phase 4 was holding at 0% strain. The same strain was applied to the collagen gels during each cycle. The control regimen was application of one cycle. The other regimens were; 4 hour (12 cycles), 8 hour (24 cycles), 16 hour (48 cycles), 24 hour (72 cycles) and 48 hour (144 cycles). Collagen gels were analysed for fibril diameter (electron microscopy) or quasi-static tensile mechanical properties directly after the treatment Transmission Electron Microscopy Routine TEM was employed to measure the changing collagen fibril diameters in cyclically loaded collagen gels. 3D collagen gels were washed in 0.1 M phosphate buffered saline (PBS), fixed in 2.5% gluteraldehyde in 0.1 M phosphate buffer for 1 h at 4° C., followed by two PBS washes and a secondary fixation with 1% osmium tetroxide in a 0.1 M cacodylate buffer, for 1 hr at room temperature. Specimens were then dehydrated through an increasing acetone series, infiltrated with acetone: araldite CY212 resin (1:1) overnight, ending with complete replacement with fresh resin through two changes, each for a minimum of 3 hrs, and polymerisation at 60° C. for 18 hrs. Ultra-thin sections (80-100 nm) were cut from trimmed blocks using a diamond knife, and stained with 2% uranyl acetate and lead citrate (10 min) and viewed on a Phillips CM12 electron microscope (Agar Scientific Ltd., Essex, UK).

Image Analysis

Samples for TEM processing were obtained from the 'alignment' zone of fixed gels, and sectioned along the transverse plane of the gels. 10 random photographs were taken per section, and the diameters of all transversely sectioned collagen fibrils were measured with Openlab™ version 3.1.5 image analysis software (Improvision®, Coventry, UK). Measurements were only valid where the Y and X dimension of the circular transverse section were equal i.e. the collagen fibril was a perfect circle, and not cut at an angle or where two or more fibrils overlapped.

Statistics

All experimental results were analysed using Graphpad Prism™ version 4 software (Graphpad Prism Software, San Diego, USA). One way ANOVA was performed on all groups, with Dunnetts multiple comparisons post-test.

Mechanical Strength Testing

Pull-out experiments were devised to test the break strength of the cyclically loaded collagen gels. First the gels were cyclically loaded, or left as controls, then using the t-CFM a steady single ramp load was applied to the gel, until it broke. The mean break force and other parameters were then calculated from the stress/strain curves.

Results

The plastic compression (PC) stage of the process described herein effectively pushes collagen fibrils into close proximity and contact with each other, promoting fibril anastomosis. The hypothetical basis of load induced (sliding) fusion is shown in FIG. 7.

Figure 1:
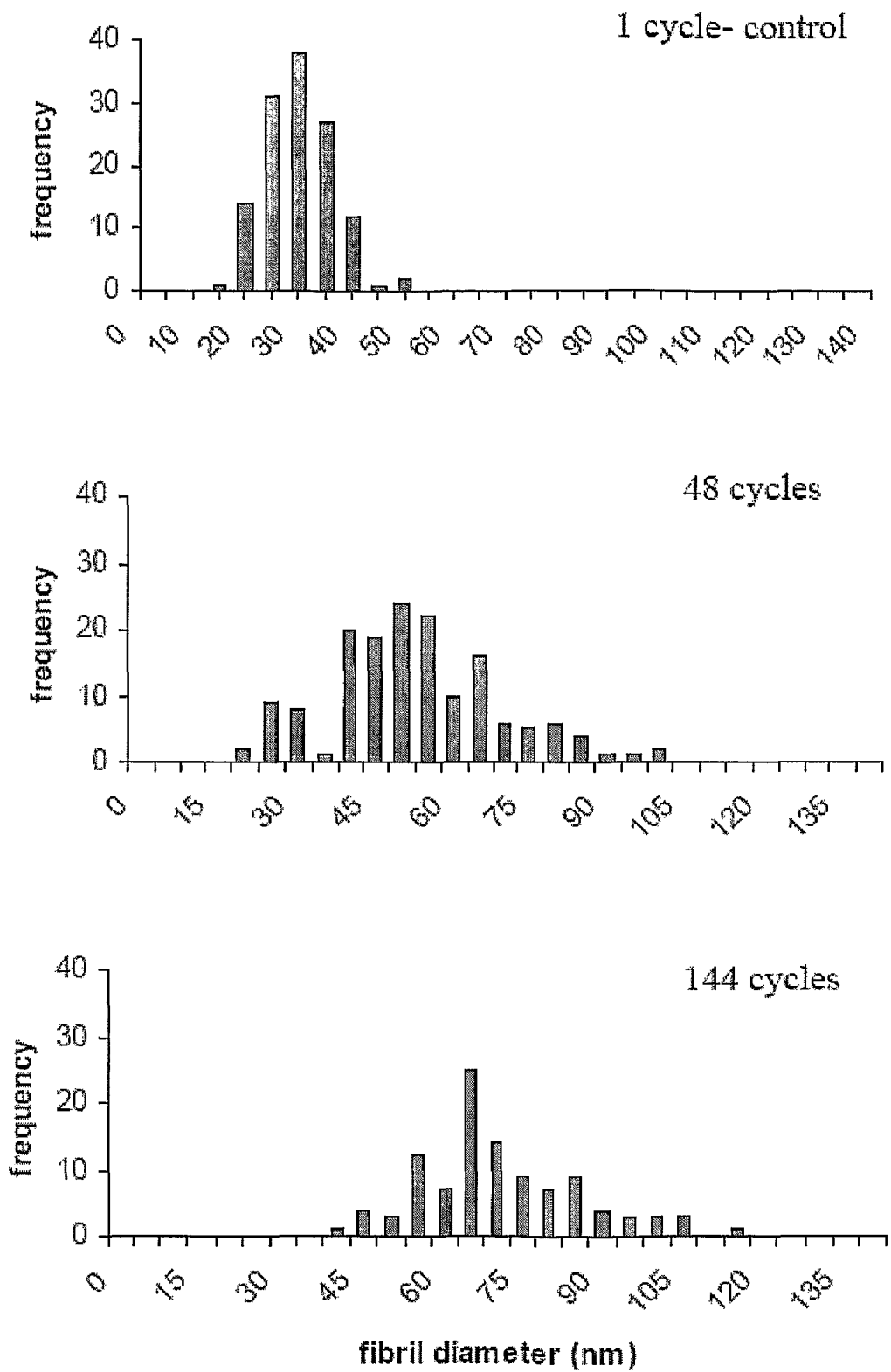

Mean collagen fibril diameters were measured from transmission electron micrographs in transverse sections of PC materials (i.e. perpendicular to the loaded axis), following 1 to 144 loading cycles. Increasing cyclical load of compressed collagen sheets was found to induce a progressive increase in inter-fibrillar contact and lateral fusion, as judged by fibril clumping and increased cross-sectional diameter in the micrographs (FIG. 1). A range of forms of fibril-fibril interaction were observed to become increasingly common with increasing number of cycles. These included simple increase in fibril cross-section diameter with symmetrical, circular cross-section, and 'dumb-bell' and 'clover leaf' shapes comprising 2 or 3 partly super-imposed fibrils in cross-section. At the earliest stage of this process, many fibrils in close proximity were observed to be linked by a thin bridge of electron dense thread material.

Figure 2:
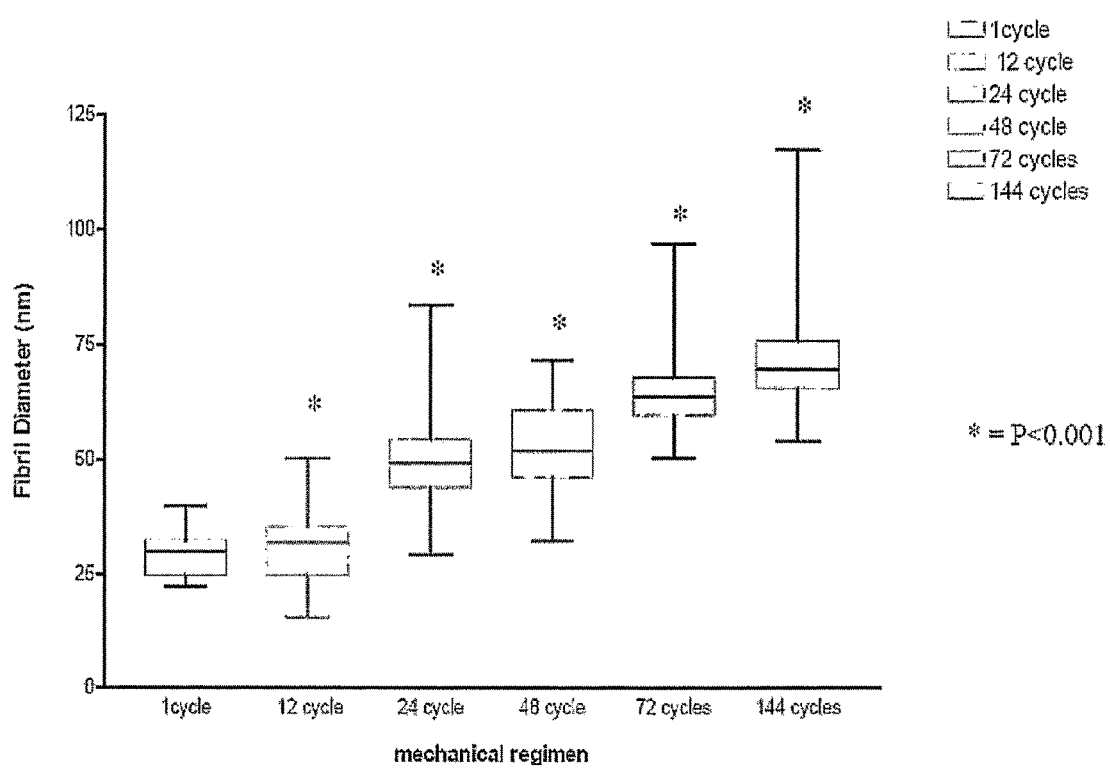
Figure 3:
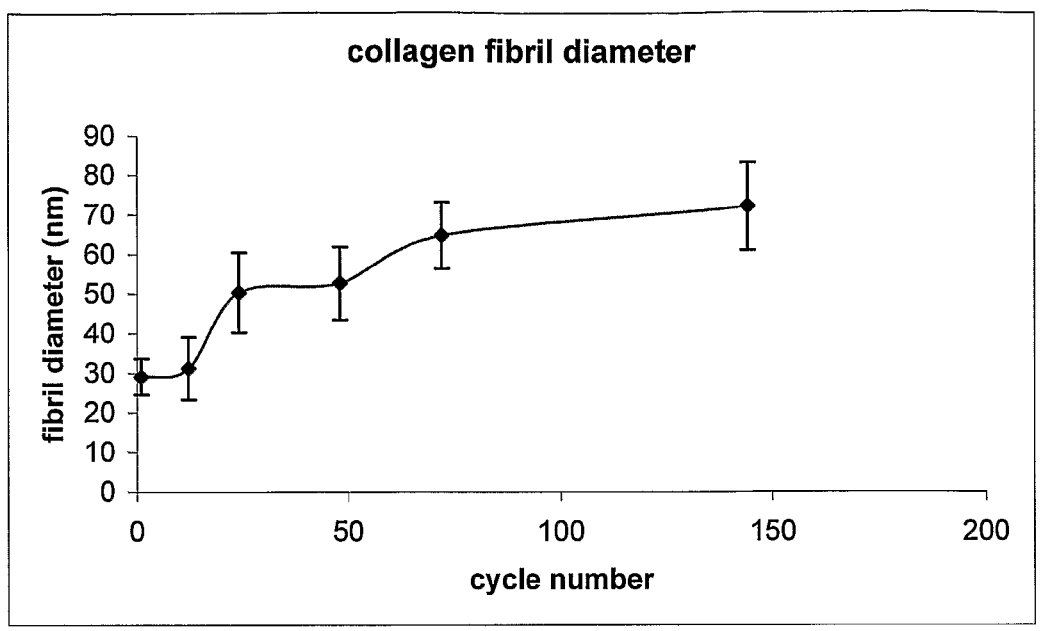
FIG. 3 shows a line plot of the increase in mean fibril diameter with increasing numbers of load cycles, showing the stepwise increase and the SD around the mean.

Direct measurement identified a clear increase in collagen fibril diameter with increasing load cycle number. Median fibril diameters from 3 replicate collagen specimens for each treatment were measured by image analysis of random TEM fields (10 fields per specimen). The median fibril diameter at 1 cycle was 29±4.6 nm and this increased significantly (>2 fold) to 70±10 nm after 144 cycles (P<0.001) (FIGS. 2 and 3). Aside from the 12-cycle regimen, the median fibril diameter for all test groups was significantly greater than the control group. There was also a clear increase in the total range of fibril diameters with increased cycling. This was mirrored by the reduced median frequency. There was, however, no difference in the range of $25^{th}$ and $75^{th}$ percentile with increased cycling.

In addition, the increase in fibril diameter progressed through a clear series of steps, seen as three steps across the six treatment groups. There was no significant difference between 1 and 12 cycles (group 1), 24 and 48 cycles (group 2) and 96 and 144 cycles (group 3). Yet, group 2 and 3 both increased progressively and significantly compared to group 1 (FIG. 2). Fibrils of 15-40 nm diameter were completely lost in later loading cycles.

Increasing fibril diameter was primarily a result of the formation of symmetrical, round cross-section fibrils not due to increasing numbers of multi-lobed structures (these were not measured as single fibrils). This provides indication that there was a substantial degree of remodelling of fibril cross-sectional shape as part of the anastomosis process. This was consistent with the appearance of linking 'strands' between close fibrils, again providing indication of surface remodelling and collagen mobility (FIG. 7).

Figure 4:
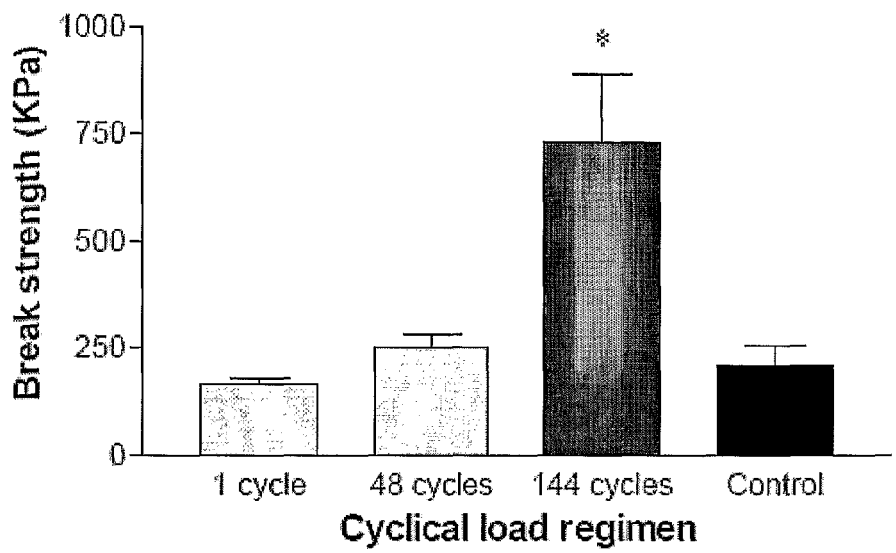
FIG. 4 shows the increasing mean break strength of collagen gels following cyclical loading. *=P<0.001.
Figure 5:
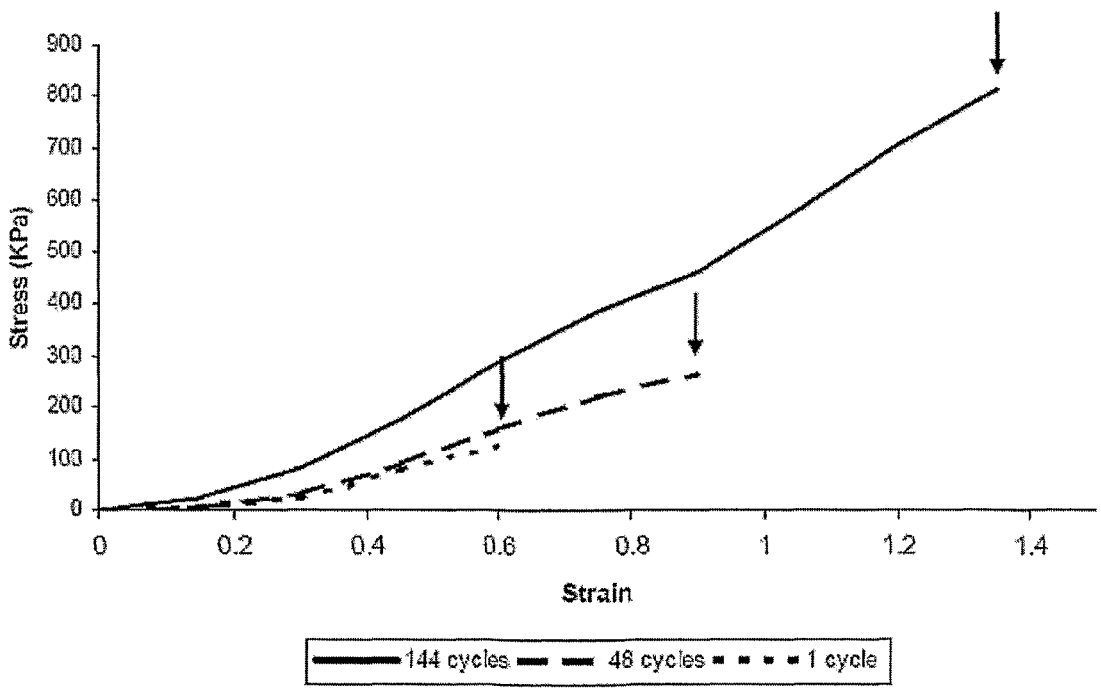
FIG. 5 shows the stress/strain relationship for collagen gels following cyclical loading indicating the far greater break stress and stiffness (increasing gradients) of loaded specimens.

The mechanical properties of cyclically loaded constructs were monitored in terms of break stress; break strain and elastic modulus (FIGS. 4 to 6). FIG. 4 shows the increase in mechanical strength which was observed with increasing number of load cycles. The break stress of collagen loaded for 144 cycles was 4.5 times greater than 1 cycle (P<0.001). Although 48 loading cycles produced an increase in mean break stress, this did not reach statistical significance. Similarly the modulus rose by 23% with 48 and 56% with 144 cycles, whilst the break strain rose to 133±35%, a two-fold increase.

A series of specimens were incubated under static 20% load for 48 hours (equivalent time period as for the 144 cycles, but without cycling). This treatment produced no increase in material break stress (FIG. 6) and indeed was the same as the 1-cycle control specimens. As a result increased mechanical strength did not relate to incubation period alone, but did correlate closely with the number of loading cycles and the resultant increase in collagen fibril diameter.

Conventional understanding of fibrous material properties indicates that increasing fibril diameter will increase overall material strength. Mechanical properties of cyclically loaded constructs were monitored by carrying out a quasi-static tensile test at the end of loading and the parameters of break strength; break strain and elastic modulus. FIG. 5 shows representative stress-strain behaviour of the gels after cyclic loading and Table 1 summarises the data obtained.

The above experimental findings show that cyclic loading of a collagen gel leads to collagen fibril fusion, which is reflected in increasing fibril diameter and a correlated increase in tensile properties. The staged diameter increase is consistent with the progressive addition of a discrete small diameter fibril. Since cell free systems were used, control of fibril diameter (and so control of resultant tissue material properties) is shown to be primarily a physio-chemical process. This provides indication that tissue properties in vivo are controlled by a combination of local, cell generated strains and external loading.

References

Ameye L, Young M F Glycobiology. 2002 September; 12(9): 107R-16R. Review.
Birk D E, et al J Cell Biol. 1988 March; 106(3):999-1008.
Birk D E et al J Cell Sci. 1990 April; 95 (Pt 4):649-57.
Brinckerhoff C E et al Nat Rev Mol Cell Biol. 2002 March; 3(3):207-14.
Canty E G et al. J Cell Sci. 2005 Apr. 1; 118(Pt 7):1341-53.
Chapman J A. Biopolymers. 1989 August; 28(8):1367-82. Erratum in: Biopolymers 1989 December; 28(12):2201-5.
Corsi A et al J Bone Miner Res. 2002 July; 17(7):1180-9.
Doane K J et al. Exp Cell Res. 1992 September; 202(1):113-24.
Ezura Y et al J Cell Biol. 2000 Nov. 13; 151(4):779-88.
Graham H K et al J Mol Biol. 2000 Jan. 28; 295(4):891-902.
Guidry C et al Coll Relat Res. 1987 February; 6(6):515-29.

Hay E D J Cell Biol. 1981 December; 91(3 Pt 2):205s-223s. Review.
Kadler K E et al Biochem J. 1996 May 15; 316 (Pt 1):1-11. Review.
Linsenmayer T F et al J Cell Biol. 1993 June; 121(5):1181-9.

TABLE 1

| Number of cycles | Break Stress (MPa) | Modulus (MPa) | Strain (Ratio) |
| --- | --- | --- | --- |
| 1 | 0.17 ± 0.03 | 0.24 ± 0.06 | 0.71 ± 0.24 |
| 48 | 0.26 ± 0.07 | 0.31 ± 0.07 | 0.90 ± 0.24 |
| 144 | 0.76 ± 0.50 | 0.54 ± 0.27 | 1.33 ± 0.35 |

TABLE 2

| | 1 cycle (control) | 12 cycle | 48 cycle | 72 cycle | 144 cycle |
| --- | --- | --- | --- | --- | --- |
| longitudinal | 20 | 20 | 15 | 17 | 17 |
| transverse | 28 | 28 | 34 | 33 | 39 |
| oblique | 52 | 52 | 51 | 50 | 44 |

The invention claimed is:

1. A method of producing a biomaterial comprising:
   (i) plastically compacting a collagen gel;
   (ii) applying a uniaxial tensile load to the compacted gel, wherein said load imparts a strain of at least 5% to the compacted gel;
   (iii) removing said load from the compacted gel, such that the strain imparted to the compacted gel is removed; and
   (iv) repeating steps (ii) and (iii) 10 or more times to produce said biomaterial.

2. A method according to claim 1, wherein said biomaterial has increased material strength relative to the compacted gel or altered fluid and solute permeability properties.

3. A method according to claim 1, wherein said biomaterial has increased fibril diameter relative to the compacted gel.

4. A method according to claim 1, wherein step (ii) comprises increasing the load applied to the gel progressively up to a pre-determined uniaxial tensile load.

5. A method according to claim 4, wherein the predetermined uniaxial tensile load subjects the compacted gel to a strain of 5-40%.

6. A method according to claim 5, wherein the load applied to the gel is increased progressively at a rate of less than 10% strain/min.

7. A method according to claim 4, wherein the predetermined load is maintained for at least 1 minute.

8. A method according to claim 1, wherein step (iii) comprises removing the load progressively from the gel.

9. A method according to claim 8, wherein the load is removed progressively at a rate of less than 10% strain/min.

10. A method according to claim 1, wherein the compacted gel is maintained unloaded for at least 1 minute following removal of the load.

11. A method according to claim 1, wherein steps (ii) and (iii) are repeated at 10 or less times per hour.

12. A method according to claim 1, wherein the gel is immersed in an aqueous liquid.

13. A method according to claim 12, wherein the liquid is a culture medium.

14. A method according to claim 1, wherein the collagen gel comprises viable cells, said cells being distributed interstitially within the collagen gel.

15. A method according to claim 14, wherein the viable cells are selected from the group consisting of muscle cells, liver cells, kidney cells, heart cells, lung cells, gut cells, bronchial cells, ocular cells, reproductive cells, vascular cells, neural cells, secretory cells, stem cells, fibroblasts, Schwann cells, smooth muscle cells, endothelial cells, urothelial cells, osteocytes, chondrocytes, and tendon cells.

16. A method according to claim 1, wherein the plastic compaction comprises a reduction in volume of said gel of at least 50%.

17. A method according to claim 1, wherein the gel is plastically compacted by applying a compressive force to the gel.

18. A method according to claim 1, wherein the fibrils of the collagen gel are aligned by applying uniaxial tension to the gel.

19. A method according to claim 18, wherein the uniaxial tension is applied before plastic compaction.

20. A method according to claim 1, comprising implanting the biomaterial in a human or animal body for the repair or replacement of damaged tissue.

21. A method according to claim 1, comprising moulding or shaping the biomaterial to produce a tissue equivalent implant.

22. A method according to claim 21, comprising folding or rolling the biomaterial to produce the implant.

23. A method according to claim 21, wherein the biomaterial is subjected to further plastic compaction to produce the implant.

* * * * *